(12) United States Patent
Schmidlin et al.

(10) Patent No.: US 11,607,486 B2
(45) Date of Patent: Mar. 21, 2023

(54) INJECTOR DEVICE (71) Applicant: Novartis AG, Basel (CH)

(72) Inventors: Alain Schmidlin, Basel (CH); Mario Iobbi, Basel (CH); Erich Studer, Basel (CH); Andrew Bryant, Basel (CH); Chinmay Deodhar, Pune (IN); Rajan Patel, Menlo Park, CA (US)

(73) Assignee: Novartis AG, Basel (CH)

( * ) Notice: Subject to any disclaimer, the term of this patent is extended or adjusted under 35 U.S.C. 154(b) by 531 days.

(21) Appl. No.: 16/494,231

(22) PCT Filed: Feb. 1, 2018

(86) PCT No.: PCT/EP2018/052482
§ 371 (c)(1),
(2) Date: Sep. 13, 2019

(87) PCT Pub. No.: WO2018/166699
PCT Pub. Date: Sep. 20, 2018

(65) Prior Publication Data
US 2020/0121848 A1 Apr. 23, 2020

Related U.S. Application Data (60) Provisional application No. 62/471,981, filed on Mar. 16, 2017.

(30) Foreign Application Priority Data

Mar. 31, 2017 (EP) ..................... 17164212

(51) Int. Cl.
A61M 5/142 (2006.01)
A61M 5/145 (2006.01)
A61M 5/158 (2006.01)

(52) U.S. Cl.
CPC ...... *A61M 5/14244* (2013.01); *A61M 5/1452* (2013.01); *A61M 2005/1426* (2013.01);
(Continued)

(58) Field of Classification Search
CPC ........... A61M 2005/1426; A61M 2005/14252; A61M 2005/14256; A61M 2005/14268;
(Continued)

(56) References Cited

U.S. PATENT DOCUMENTS 3,583,399 A 6/1971 Ritsky
5,957,889 A 9/1999 Poulsen et al.
(Continued)

FOREIGN PATENT DOCUMENTS

CN 102149416 A 8/2011
EP 3106190 A1 12/2016
(Continued)

OTHER PUBLICATIONS

"Using RFID to Track Critical Medical Device Information: Vizinex." Vizinex RFID, Jul. 7, 2015, (6 pages), https://web.archive.org/web/20150711212300/https://www.vizinexrfid.com/using-rfid-track-critical-medical-device-information/.
(Continued)

*Primary Examiner* — Quynh-Nhu H. Vu
(74) *Attorney, Agent, or Firm* — Moore & Van Allen, PLLC; Henry B. Ward, III (57) ABSTRACT The invention concerns an injector device (100), comprising access means (110, 115) configured to selectively allow and prevent a cartridge (120) storing a pharmaceutical product (122) from being removed from the injector device (100), a self-test unit (130) configured to cause a self-test of at least one of an electronic component and an electronic assembly of the injector device (100), and a control unit (140) configured to control the access means (110, 115) to allow the
(Continued)

cartridge (120) to be removed from the injector device (100) in case the self-test has failed.

14 Claims, 8 Drawing Sheets

(52) U.S. Cl.
CPC ............ *A61M 2005/14268* (2013.01); *A61M 2005/1585* (2013.01); *A61M 2205/13* (2013.01); *A61M 2205/3569* (2013.01); *A61M 2205/702* (2013.01); *A61M 2205/8206* (2013.01)

(58) Field of Classification Search
CPC ...... A61M 2005/1585; A61M 2205/13; A61M 2205/17; A61M 2205/3569; A61M 2205/702; A61M 2205/8206; A61M 5/14244; A61M 5/1452
See application file for complete search history.

(56) References Cited

U.S. PATENT DOCUMENTS

| | | | |
|---|---|---|---|
| 8,035,517 B2 | 10/2011 | Gibson | |
| 8,123,724 B2 | 2/2012 | Gillespie, III | |
| 8,446,280 B2 | 5/2013 | Ortenzi et al. | |
| 9,452,267 B2 | 9/2016 | Reynolds et al. | |
| 9,789,245 B2 | 10/2017 | Tieck et al. | |
| 2007/0197968 A1* | 8/2007 | Pongpairochana | A61M 5/20 604/67 |
| 2010/0160857 A1 | 6/2010 | Pongpairochana et al. | |
| 2011/0166512 A1* | 7/2011 | Both | A61M 5/14248 604/152 |
| 2011/0264033 A1 | 10/2011 | Jensen et al. | |
| 2011/0306929 A1 | 12/2011 | Levesque et al. | |
| 2011/0313395 A1 | 12/2011 | Krulevitch et al. | |
| 2013/0211330 A1 | 8/2013 | Pedersen et al. | |
| 2013/0225945 A1 | 8/2013 | Prince et al. | |
| 2014/0142507 A1 | 5/2014 | Armes | |
| 2015/0001285 A1 | 1/2015 | Halbert et al. | |
| 2015/0045729 A1* | 2/2015 | Denzer | A61M 5/20 604/110 |
| 2015/0126926 A1 | 5/2015 | Giambattista et al. | |
| 2015/0246176 A1 | 9/2015 | Navarro et al. | |
| 2015/0273151 A1* | 10/2015 | McLoughlin | A61M 5/002 604/66 |
| 2015/0310185 A1 | 10/2015 | Shah | |
| 2015/0328404 A1* | 11/2015 | Murakami | A61M 5/347 604/67 |
| 2016/0051750 A1 | 2/2016 | Tsoukalis | |
| 2016/0082182 A1 | 3/2016 | Gregory et al. | |
| 2016/0175515 A1 | 6/2016 | McCullough | |
| 2017/0143902 A1 | 5/2017 | Hansen et al. | |
| 2017/0281877 A1* | 10/2017 | Marlin | A61M 5/3234 |
| 2019/0167894 A1* | 6/2019 | Barchen | A61M 5/1456 |
| 2020/0238003 A1* | 7/2020 | Yigal | A61M 5/14566 |

FOREIGN PATENT DOCUMENTS

| | | |
|---|---|---|
| FR | 2217026 A1 | 9/1974 |
| GB | 143084 A | 5/1920 |
| GB | 2145795 A | 4/1985 |
| JP | 2009525111 A | 7/2009 |
| JP | 2014516634 A | 7/2014 |
| JP | 2012501771 A | 1/2021 |
| RU | 2015129763 A | 1/2017 |
| WO | WO-2005072795 A2 | 8/2005 |
| WO | 2014091765 A1 | 6/2014 |
| WO | WO-2016033496 A1 | 3/2016 |

OTHER PUBLICATIONS

Center for Devices and Radiological Health. "Radio Frequency Wireless Technology in Medical Devices—Guidance." U.S. Food and Drug Administration, FDA, Aug. 14, 2013, (24 pages), https://www.fda.gov/regulatory-information/search-fda-guidance-documents/radio-frequency-wireless-technology-medical-devices-guidance-industry-and-fda-staff.

Fujitsu, "Application: Fujitsu RFID and Sensor Solution for Medical Device Traceability," https://www.fujitsu.com/us/Images/FUJITSU%20RFID%20for%20Medical%20Device%20Traceability.pdf, Aug. 2015, 2 pages.

International Search Report issued by the European Patent Office for International Patent Application No. PCT/EP2018052482 dated Mar. 16, 2018.

Written opinion issued by the European Patent Office for International Patent Application No. PCT/EP2018052482 dated Mar. 16, 2018.

International Preliminary Report on Patentability issued by the European Patent Office for International Patent Application No. PCT/EP2018052482 dated Sep. 17, 2019.

Office Action issued by the Japanese Patent Office for Japanese Patent Application No. 2019-550828, dated Oct. 4, 2021.

Office Action issued by the Russian Patent Office for Russian Patent Application No. 2019127652/14(054259), dated Jun. 1, 2021.

Search Report issued by the Russian Patent Office for Russian Patent Application No. 2019127652/14(054259), dated Jun. 1, 2021.

Office Action related to Chinese Patent Application No. 201880018546.6, dated Feb. 22, 2022.

Office Action issued by the Korean Patent Office for Korean Patent Application No. 10-2019-7026778, dated Sep. 28, 2022.

* cited by examiner

INJECTOR DEVICE

CROSS REFERENCE TO RELATED APPLICATIONS

This application is a national stage entry, filed under 35 U.S.C. 371, of International Application No. PCT/EP2018/052482, filed on Feb. 1, 2018, which claims the benefit of and priority to U.S. Provisional Application No. 62/471,981, filed Mar. 16, 2017, and claims the benefit of and priority to European Patent Application No. 17164212.7, filed Mar. 31, 2017, the entire contents of which are hereby incorporated herein by reference in their entireties and for all purposes.

The invention relates to an injector device. In particular, the invention relates to safety aspects of an injector device.

An injector device is a medical device designed to apply a pharmaceutical product via injection to a human or animal body. For safety reasons, it has to be ensured that the injector device operates correctly.

WO 2016/033496 A1 concerns automatic injection devices for drug delivery which incorporate an electronic skin sensor that is used as an input to a drive control mechanism. The status of the electronic skin sensor is used to enable and disable functions of the drive control mechanism and to activate functions of the drive control mechanism. However, problems may arise in case the electronic skin sensor malfunctions and a wrong status of the electronic skin sensor is used to enable and disable functions of the drive control mechanism and to activate functions of the drive control mechanism.

The invention is directed at the object of providing an injector device having improved safety capabilities.

This object is addressed by the injector device as defined in claim 1.

The injector device comprises access means configured to selectively allow and prevent a cartridge from being removed from the injector device, a self-test unit configured to cause a self-test of at least one of an electronic component and an electronic assembly of the injector device, and a control unit configured to control the access means to allow the cartridge to be removed from the injector device in case the self-test has failed.

The cartridge is a container that accommodates a pharmaceutical product and is adapted to dispense the pharmaceutical product by means of the injector device. The term "pharmaceutical product" is meant to encompass any medicament-containing flowable drug configured to be passed through a hollow needle of the injector device in a controlled manner, such as a liquid, solution, gel or fine suspension.

The access means may comprise any mechanical element or structure that allows a cartridge to be inserted in and removed from the injector device. For example, the access means may comprise a door or a shutter that can be locked or unlocked so that after the door or shutter is unlocked, the cartridge can be inserted in and removed from the injector device. In a preferred embodiment, the access means comprise a cartridge receiving unit configured to receive and hold a cartridge, wherein the cartridge receiving unit is configured to at least partially protrude from a housing of the injector device so that a cartridge held in the cartridge receiving unit can be removed from the injector device. The protrusion of the cartridge receiving unit from the housing of the injector device may comprises a rotating or sliding mechanism that rotates or slides the cartridge receiving unit from a closed state to an opened state, and vice versa.

In a preferred embodiment, the access means comprise drive means adapted to cause the access means to be transitioned from a state where the cartridge cannot be inserted into the injection device to a state where the cartridge can be inserted into the injection device. For example, the drive means may comprise an electric motor which causes a force to open a door, a shutter, or a cartridge receiving unit. In particular, the electric motor may cause a biased spring to release its spring force so that a door, a shutter, or a cartridge receiving unit is automatically opened.

The self-test unit may comprise any kind of processing unit that is adapted to test at least one of an electronic component and an electronic assembly of the injector device. For example, the self-test unit may comprise a microprocessor running a software that checks whether the at least one of an electronic component and an electronic assembly provides appropriate response signals when sending control signals to them.

In a preferred embodiment, the at least one of an electronic component and an electronic assembly of the injector device comprises at least one of an electric motor, a near field communication system, a battery, a proximity sensor, a processor, a needle ejection mechanism, and a needle retraction mechanism. For example, the self-test unit may be configured to perform a power-on self-test, a periodic test checking whether the device has not become unsafe since the power-on self-test, and/or individual tests checking whether the sensors and/or actuators of the injector device operate correctly.

The control unit may be any kind of electronic control means, for example a microprocessor, configured to control the access means to allow the cartridge to be removed from the injector device in case the self-test has failed.

In a preferred embodiment, the control unit controls the access means such that the injector device is automatically transitioned into a state where the cartridge can be removed from the injector device. For example, when the self-test has failed, the control unit may cause a door or a shutter to automatically open so that the cartridge may be removed from the injector device. Moreover, in case the access means comprises a cartridge receiving unit configured to receive and hold a cartridge, the control unit may be configured to cause the cartridge receiving unit to automatically at least partially protrude from a housing of the injector device so that a cartridge held in the cartridge receiving unit can be removed from the injector device when the self-test has failed.

In one embodiment, the control unit is configured to obtain cartridge data regarding a cartridge that is inserted in the injector device, check whether the cartridge data indicates that the inserted cartridge is not to be used with the injector device, and control the access means to allow the cartridge to be removed from the injector device in case the checked cartridge data indicates that the inserted cartridge is not to be used with the injector device. For this, the cartridge may comprise a communication tag, for example, a near-field communication (NFC) tag storing information regarding the pharmaceutical product (e.g., product name, batch number, expiry date, etc.). The injector device may comprise corresponding reading means, for example, an NFC reader unit, adapted to wirelessly read the information stored in the communication tag. For example, in case the checked cartridge data indicates that the pharmaceutical product has expired, a door of the injector device may automatically open to allow the user to remove the cartridge from the injector device.

In a further preferred embodiment, the injector device comprises a cartridge detector configured to determine whether a cartridge is inserted in the injector device, wherein the control unit is configured to control the access means to allow a cartridge to be inserted in the injector device in case the cartridge detector has determined that no cartridge is inserted in the injector device. The cartridge detector may be any kind of switch or sensor that is adapted to determine whether a cartridge is inserted in the injector device. For example, the cartridge detector may be an NFC reader unit adapted to read an NFC tag that is provided on the cartridge. In case no information stored on the NFC tag can be read by the NFC reader, the cartridge detector assumes that no cartridge is inserted in the injector device. In this case, the access means allows a cartridge to be inserted in the injector device, e.g., by automatically opening a cartridge receiving unit.

In a further preferred embodiment, the control unit is configured to control the access means to prevent the cartridge from being removed from the injector device in case the self-test was successful and the checked cartridge data indicates that the inserted cartridge can be used with the injector device. In case these conditions are fulfilled, it may be assumed that the injector device is in a state ready to be operated. For example, a door, shutter, or cartridge receiving unit can be locked in case the self-test was successful and the checked cartridge data indicates that the inserted cartridge can be used with the injector device.

In one embodiment, the injector device further comprises a hollow skin needle configured to be ejected from the injector device, a proximity sensor configured to generate a proximity signal indicating that the injector device is placed on a skin of a human or animal body, and ignition means configured to generate an ignition signal indicating that a user of the injector device has triggered an injection by the injector device. The hollow skin needle is adapted to puncture the skin of a human or animal body. Through the hollow skin needle, the pharmaceutical product accommodated in the cartridge can be dispensed in the human or animal body. The proximity sensor preferably uses a capacitive sensing technology for determining a distance between the proximity sensor and the skin of the human or animal body. The control unit may process the distance data from the proximity sensor for determining whether the injector device has been placed on the skin of the human or animal body. The ignition means may be a switch or a button provided on the surface of the injector device that can be operated by the user of the injector device in order to start the injection of the injector device.

To prevent a misinterpretation of a situation in which a user holds the injector device in his/her hand for loading the cartridge into the injector device and at the same time blocks with his/her fingers an opening or openable element through which the skin needle is to be ejected from the injector device, the control unit may be configured to not cause an ejection of the skin needle from the injector device in case the control unit has obtained the proximity signal and the ignition signal, and the proximity signal has been continuously obtained from a power-on of the injector device until the ignition signal has been obtained. In this situation, the injector device may only start operation after the user has once removed his/her fingers from the opening or openable element through which the skin needle is ejected from the injector device, which causes an interruption of the proximity signal. The power-on of the injector device may be an initial supply of the electric components of the injector device with power, or an event that causes the injector device to start operation, e.g., a closing of a door, a shutter, or a cartridge receiving unit after a cartridge has been inserted in the injector device.

To prevent a misinterpretation of a situation in which a user accidently blocks with his/her fingers an opening or openable element through which the skin needle is to be ejected from the injector device, the control unit may be configured to not cause an ejection of the skin needle from the injector device in case the control unit has obtained the proximity signal and the ignition signal, and the ignition signal has been obtained within a predetermined period of time after the proximity signal has been obtained. In a preferred embodiment, the predetermined period of time is approximately one second. Thus, in case the proximity signal is not received for a continuous period of time that is longer than approximately one second, the control unit assumes that the user has accidently blocked with his/her fingers the opening or openable element through which the skin needle is to be ejected.

To prevent a misinterpretation of a situation in which a user accidently blocks with his/her fingers an opening or openable element through which the skin needle is to be ejected from the injector device when he/she closes a door, a shutter, or a cartridge receiving unit of the injector device, the control unit may be configured to not cause an ejection of the skin needle from the injector device in case the control unit has obtained the proximity signal and the ignition signal, and the proximity signal has been obtained within a predetermined period of time after a point of time when the access means has prevented a cartridge from being removed from the injector device. In a preferred embodiment, the predetermined period of time is approximately two seconds. For example, the control unit may ignore a proximity signal that is received within approximately two seconds after a door, a shutter, or a cartridge receiving unit of the injector device has been closed. For this, the injector device may comprise a determining unit configured to determine whether the door, shutter, or cartridge receiving unit has been closed.

In order to enable a more precise determination whether the injector device has been placed on the skin of a human or animal body, the injector device may comprise a first proximity sensor configured to generate a first proximity signal indicating that the injector device is placed on a skin of a human or animal body, and a second proximity sensor configured to generate a second proximity signal indicating that the injector device is placed on a skin of a human or animal body, wherein the control unit is configured to determine that the injector device has been placed on a skin of a human or animal body based on the first proximity signal and the second proximity signal.

In a preferred embodiment, the control unit is configured to determine that the injector device has been placed on a skin of a human or animal body when the first proximity signal and the second proximity signal are obtained at the same time. In particular, if only one of the first proximity signal and the second proximity signal are obtained at the same time, the control unit assumes that the injector device is not correctly placed on the skin of the human or animal body, for example, only one area of a bottom side of the injector device is placed on the skin of the human or animal body.

In order to enable an improved determination whether the injector device is correctly placed on the skin of the human or animal body, a virtual line connecting the first proximity sensor and the second proximity sensor does not cross the skin needle in its ejected state.

Preferably, the first proximity sensor and the second proximity sensor may be located with the same distance from the skin needle.

Further preferably, the first proximity sensor and the second proximity sensor may be located closer to the center of the injector device than the skin needle.

In one embodiment, the control unit is configured to determine based on the first proximity signal and the second proximity signal whether the injector device has been removed from the skin of the human or animal body, and cause a retraction of the skin needle into the injector device in response to the determination that the injector device has been removed from the skin of the human or animal body. In case of this determination, the control unit may cause further operations within the injector device, for example, an interruption of the dispensing of the pharmaceutical product from the cartridge.

In a further preferred embodiment, the injector device comprises a septum needle configured to pierce a septum of a cartridge inserted into the injector device. In order to avoid that the pharmaceutical product gets clogged in the hollow skin needle, the septum needle, and/or any fluid path connecting the cartridge with the hollow skin needle, the control unit may be configured to cause the ejection of the skin needle and the piercing of the septum by the septum needle immediately before or simultaneously with the ejection of the skin needle.

Preferred embodiments of the invention will now be described in greater detail with reference to the appended schematic drawings, wherein.

Figure 1:
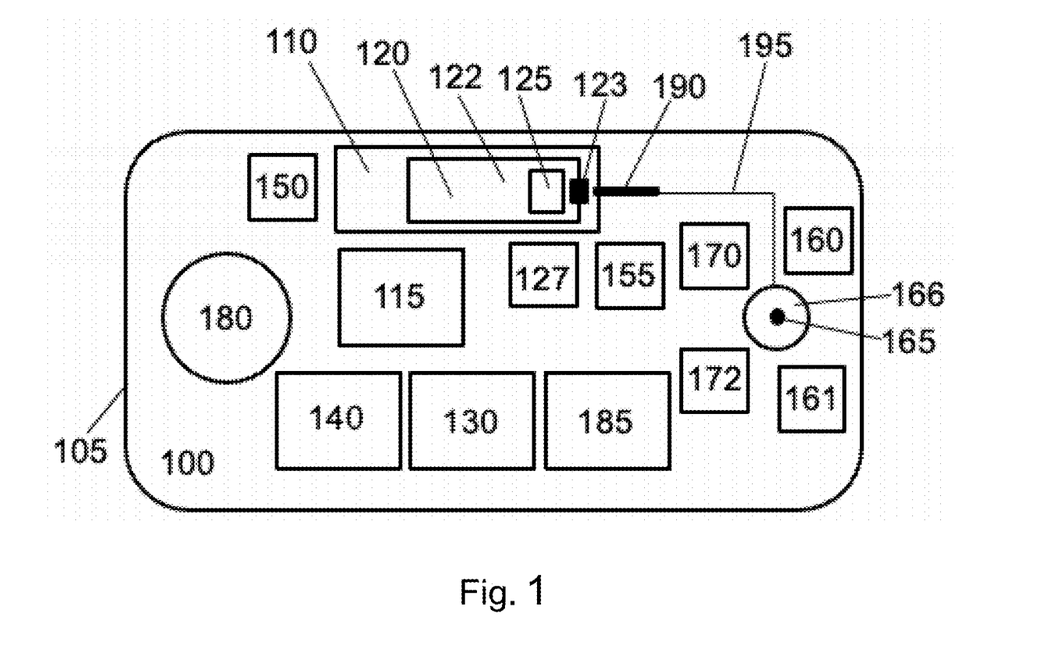
FIG. 1 schematically shows a first embodiment of an injector device.

FIG. 1 schematically shows a first embodiment of an injector device 100. The injector device 100 is adapted to be loaded with a cartridge 120 in which a pharmaceutical product 122 is accommodated. For this, the injector device comprises a cartridge receiving unit 110. The cartridge 120 can be inserted in the cartridge receiving unit 110, which can be opened and closed (not shown in FIG. 1) so that the cartridge 120 can be inserted in and removed from the cartridge receiving unit 110.

The injector device 100 is further equipped with a needle ejection mechanism 160 and a needle retraction mechanism 161. The needle ejection mechanism 160 is adapted to eject a hollow skin needle 165 from the injector device, and the needle retraction mechanism 161 is adapted to retract the ejected skin needle 165 into the injector device. The skin needle 165 is housed inside the housing 105 of the injector device 100. Upon pressing of an ignition button 180 by a user, the needle ejection mechanism 160 ejects the skin needle 165 out of the housing 105 and dispenses the pharmaceutical product 122 from the cartridge 120 through the hollow skin needle 165. For this, the housing 105 comprises an opening 166 through which the skin needle 165 can be ejected out of the housing 105. Additionally, an openable element (for example, a door) may cover the opening 166.

Thus, a user of the injector device 100 may operate the injector device 100 as follows: he/she can open the cartridge receiving unit 110, can insert a cartridge 120 into the opened cartridge receiving unit 110 or remove a cartridge 120 from the opened cartridge receiving unit 110, can close the cartridge receiving unit 110 (with or without a cartridge 120 inserted into the cartridge receiving unit 110), can place the injector device 100 on the skin of a human or animal body, and can press the ignition button 180 in order to start the operation of the injector device 100.

Since an ejection of a sharp skin needle 165 is concerned, the injector device 100 has to be equipped with sophisticated safety mechanisms. Moreover, since the pharmaceutical product 122 accommodated in the cartridge 120 may have a high cost, it should be ensured that the cartridge 120 is only unsealed in case the injector device 100 is in a condition to carry out the entire needle ejection-, pharmaceutical product dispensing-, and needle retraction-process.

To explain in more detail with reference to FIG. 1, the injector device 100 further comprises drive means 115, a self-test unit 130, a control unit 140, a cartridge detector 150, a cartridge receiving unit detector 155, an NFC reader unit 127, a first proximity sensor 170, a second proximity sensor 172, a battery 185 powering the electric elements of the injector device 100, a hollow septum needle 190, and a fluid path 195.

The control unit 140 controls the operation of the injector device 100. For this, the control unit 140 may be realized as a microprocessor which is adapted to receive signals from and send control signals to the drive means 115, the self-test unit 130, the cartridge detector 150, the cartridge receiving unit detector 155, the NFC reader unit 127, the first proximity sensor 170, and the second proximity sensor 172.

The cartridge 120 comprises at one end a septum 123 that can be pierced by the hollow septum needle 190. When the septum 123 is pierced by the septum needle 190, the pharmaceutical product 122 accommodated in the cartridge 120 can flow from a dispensing port of the cartridge 120 through the septum needle 190 and the fluid path 195 to the hollow skin needle 165. For forcing the pharmaceutical product 122 out of the cartridge 120, the cartridge 120 comprises a piston (not shown in FIG. 1) that is axially movable within the cartridge 120. A plunger (not shown in FIG. 1) driven by the drive means 115 under control of the control unit 140 causes the piston to force the pharmaceutical product 122 out of the cartridge 120.

The cartridge 120 further comprises an NFC tag 125. The NFC tag 125 may be wrapped around the cartridge 120. The NFC tag 125 stores information regarding the pharmaceutical product 122 (e.g., product name, batch number, expiry date, etc.). The NFC reader unit 127 is adapted to wirelessly read the information stored in the NFC tag 125 and provide the information to the control unit 140. For example, the control unit 140 may receive information from the NFC reader unit 127 that the pharmaceutical product 122 accommodated in the cartridge 120 has expired, and forward this information to the control unit 140. Based on the received information, the control unit 140 controls the injector device 100.

The drive means 115 may be any actuator that is adapted to directly or indirectly drive mechanical elements of the injector device 100. Preferably, the drive means 115 comprises an electric motor, e.g., a direct current (DC) electric motor that is controlled by a motor control unit via a pulse-width modulation (PWM) control scheme. For example, the drive means 115 may cause the needle ejection mechanism 160 to eject the skin needle 165, and may cause the needle retraction mechanism 161 to retract the ejected skin needle 165. Furthermore, the drive means 115 may cause the septum needle 190 to pierce the septum 123. Moreover, the drive means 115 may cause the cartridge receiving unit 110 to be opened and closed.

The cartridge detector 150 is adapted to determine whether a cartridge 120 is inserted in the cartridge receiving unit 110. For this, the cartridge detector 150 may be realized as a switch which is pushed when the cartridge 120 is inserted into the cartridge receiving unit 110. Alternatively, the cartridge detector 150 may be realized in the same way as the reader unit 127, or may be incorporated in the reader unit 127, so that only when the information stored in the NFC tag 125 can be read, it is assumed that a cartridge 120 is inserted in the cartridge receiving unit 110. The cartridge detector 150 then provides the determined information to the control unit 140.

The cartridge receiving unit detector 155 may be a sensor or switch that is adapted to detect when the cartridge receiving unit 110 has been closed, i.e., has been transitioned from an opened state into a closed state. In this case, the cartridge receiving unit detector 155 sends a respective signal to the control unit 140.

Each of the first proximity sensor 170 and the second proximity sensor 172 uses a capacitive sensing technology for generating proximity signals which indicate a distance between the proximity sensor and the skin of a human or animal body. The first proximity sensor 170 provides a first proximity signal to the control unit 140, and the second proximity sensor 172 provides a second proximity signal to the control unit 140. The control unit 140 is configured to determine whether the injector device 100 has been placed on a skin of a human or animal body based on the first proximity signal and the second proximity signal, for example, when the first proximity signal and the second proximity signal are obtained at the same time. Moreover, based on the first proximity signal and the second proximity signal, the control unit 140 may determine whether the injector device 100 has been removed from the skin of the human or animal body. In this case, the control unit 140 may cause the needle retraction unit 161 to retract the skin needle 165 back into the injector device 100.

The self-test unit 130 is configured to cause a self-test of at least one of an electronic component and an electronic assembly of the injector device 100. In particular, the self-test unit 130 may test whether any one of the drive means 115, the control unit 140, the cartridge detector 150, the cartridge receiving unit detector 155, the NFC reader unit 127, the first proximity sensor 170, the second proximity sensor 172, and the battery 185 operate correctly. In case a self-test has failed, the self-test unit 130 provides this information to the control unit 140. The control unit 140 may then cause the cartridge receiving unit 110 to be opened so that the cartridge 120 can be removed from the cartridge receiving unit 110.

For example, in case the first proximity sensor 170 has a malfunction and sends a faulty first proximity signal to the control unit 140, there is a risk that during ejection of the skin needle 165 into the skin of a human or animal body, the first proximity sensor 170 sends the first proximity signal to the control unit 140 indicating that the injector device 100 has been removed from the skin of the human or animal body. This determination that the injector device has been removed from the skin of the human or animal body would cause a retraction of the skin needle 165 into the housing 105 and an abortion of the dispensing of the pharmaceutical product 122 into the skin of the human or animal body, although the injector device 100 is correctly placed on the skin of the human or animal body. To avoid such a situation, in case a self-test of the first proximity sensor 170 has failed, the self-test unit 130 sends respective information to the control unit 140. The control unit 140 then causes the cartridge receiving unit 110 to be opened so that the cartridge 120 can be removed from the cartridge receiving unit 110 and the injection operation is not started until the first proximity sensor 170 passes the self-test. Moreover, it is possible that the operation of the injector device 100 is permanently disabled after a self-test has failed. In this case, the injector device 100 may only be operated again after the manufacturer of the injector device 100 has unlocked the device.

As another example, in case the information stored in the NFC tag 125 indicates that the cartridge 120 should not be used with the injector device 100 (e.g., because the pharmaceutical product 125 does not match the setup of the injector device 100), the control unit 140 may cause the cartridge receiving unit 110 to open so that the cartridge 120 can be removed from the cartridge receiving unit 110 and replaced by a correct cartridge 120.

Thus, when a user has pushed the ignition button 180, the control unit 140 may only initiate the injection after it has positively evaluated the data received from the self-test unit 130, the cartridge detector 150, the cartridge receiving unit detector 155, the first proximity sensor 170, the second proximity sensor 172, and the information read by the NFC reader unit 127. Moreover, in case the control unit 140 has positively evaluated the data received from the self-test unit 130, the cartridge detector 150, the cartridge receiving unit detector 155, the first proximity sensor 170, the second proximity sensor 172, and the information read by the NFC reader unit 127, it may cause the cartridge receiving unit 110 to be locked so that the cartridge receiving unit 110 cannot be opened by a user.

A plurality of further safety schemes/mechanisms may be included in the injector device 100 in order to ensure that a user is not accidently pierced by the skin needle 165.

In particular, to prevent a misinterpretation of a situation in which a user holds the injector device 100 in his/her hand for loading the cartridge 120 into the injector device 100 and at the same time blocks with his/her fingers the opening 166 through which the skin needle 165 is to be ejected from the injector device 100, the control unit 140 does not cause an ejection of the skin needle 165 in case the control unit 140 has obtained the first proximity signal, the second proximity signal and an ignition signal from the ignition button 180, and the first proximity signal and the second proximity signal have been continuously obtained from a power-on of the injector device 100 until the ignition signal has been obtained. In this case, the injector device 100 may only start operation after the user has once removed his/her fingers from the opening 166 through which the skin needle 165 is ejected from the injector device 100 so that receipt of the first proximity signal and the second proximity signal is once interrupted.

Furthermore, to prevent a misinterpretation of a situation in which a user accidently blocks with his/her fingers the opening 166 through which the skin needle 165 is to be ejected from the injector device 100, the control unit 140 does not cause an ejection of the skin needle 165 in case the control unit 140 has obtained the first proximity signal, the second proximity signal and the ignition signal from the ignition button 180, and the ignition signal has been obtained within a predetermined period of time, e.g., one second, after the first proximity signal and the second proximity signal have been obtained. In this case, the control unit 140 assumes that the user has accidently blocked the opening 166 with his/her fingers.

Moreover, to prevent a misinterpretation of a situation in which a user accidently blocks with his/her fingers the opening 166 through which the skin needle 165 is to be ejected from the injector device 100 when he/she closes the cartridge receiving unit 110, the control unit 140 does not cause an ejection of the skin needle 165 in case the control unit 140 has obtained the first proximity signal, the second proximity signal and the ignition signal from the ignition button 180, and the first proximity signal and the second proximity signal have been obtained within a predetermined period of time, e.g., two seconds, after a point of time, when the cartridge receiving unit 110 has been closed. In this case, the closing of the cartridge receiving unit 110 is signaled by the cartridge receiving unit detector 155 to the control unit 140.

Another safety aspect of the injector device 100 concerns clogging of the pharmaceutical product 122. Since the pharmaceutical product 122 is a flowable drug, such as a liquid, solution, gel or fine suspension, when the pharmaceutical product 122 is dispensed from the container 120 into the septum needle 190, the fluid path 195 and the skin needle 165 without being dispensed out of the tip end of the skin needle 165, the pharmaceutical product 122 may get clogged, which may block any of the septum needle 190, the fluid path 195 and the skin needle 165, and cause a malfunction of the injector device 100. To prevent such a problem, the control unit 140 causes the needle ejection mechanism 160 to eject the skin needle 165 and the piercing of the septum 123 by the septum needle 190 immediately before or simultaneously with the ejection of the skin needle 165. Thus, only when the skin needle 165 is actually ejected from the injector device 100, the seal 123 of the cartridge 120 is broken. For example, in case a user presses the ignition button 180, however, the injection does not start because the self-test unit 130 has determined that a self-test has failed, the cartridge 120 may be removed from the opened cartridge receiving unit 110 and used later since the septum needle 190 has not pierced the septum 123.

FIGS. 2 to 6 schematically show a second embodiment of an injector device 100a. The same reference numbers concern the same elements so that any repeated explanation thereof is omitted. Specifically, the injector device 100a of the second embodiment may be the injector device 100 of the first embodiment.

Figure 2:
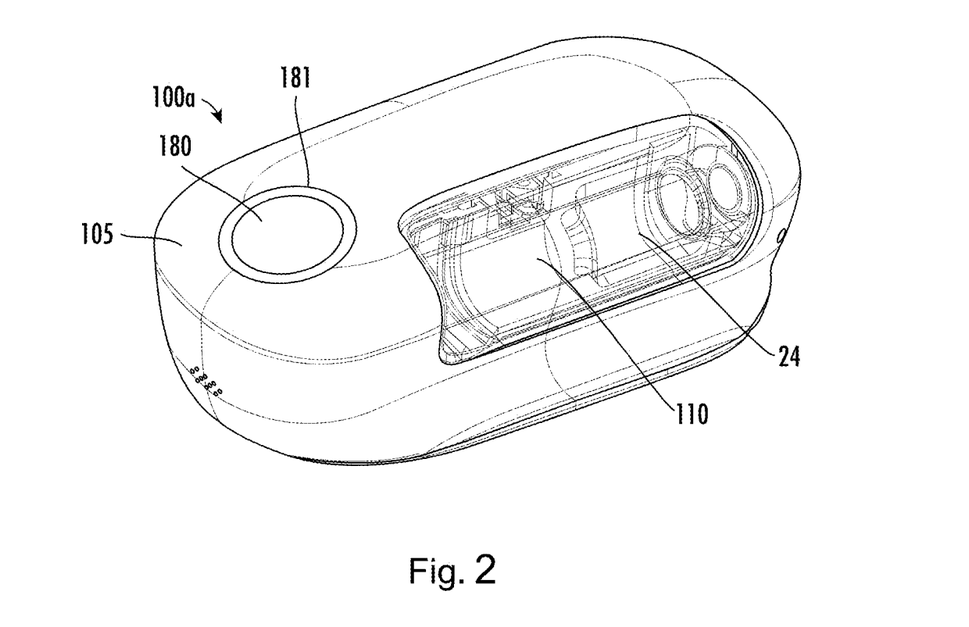
FIGS. 2 to 6 schematically show a second embodiment of an injector device.

FIG. 2 shows the injector device 100a in the closed state of the cartridge receiving unit 110. The housing 105 of the injector device 100a is shaped like a computer mouse and has a flat bottom site through which the skin needle 165 is ejected (not shown in FIG. 2) so that the injector device 100a can be stably placed on the skin of a human or animal body. Around the ignition button 180, a lightening element 181 is provided. The lightening element 181 shows a red light in case the injector device 100a is not ready for injection, and shows a green light in case the injector device 100a is ready for injection.

In the cartridge receiving unit 110, an opening 24 is provided through which a user may rotate the cartridge 120 in case a printed label provided on the cartridge 120 cannot be seen from the outside (not shown in FIG. 2).

Figure 3:
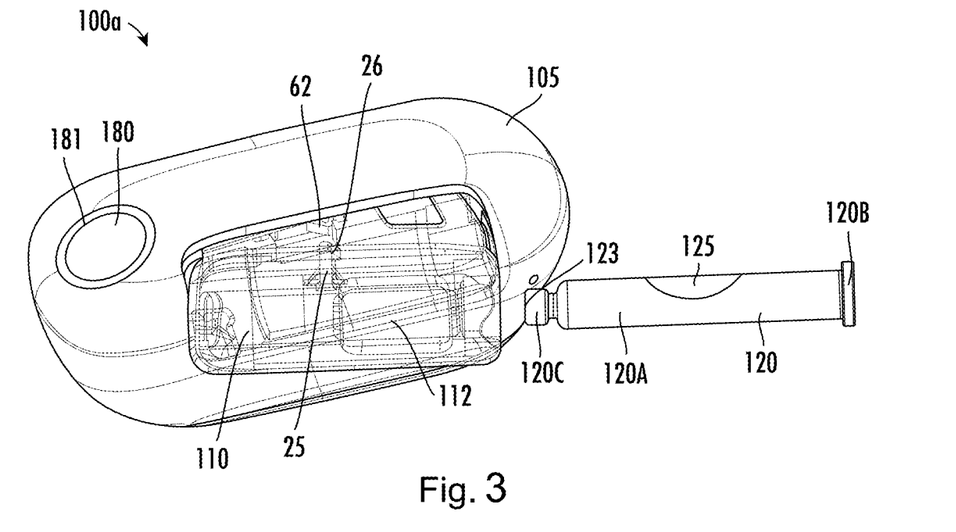

FIG. 3 shows the cartridge receiving unit 110 in the opened state before the cartridge 120 is inserted into the cartridge receiving unit 110. The cartridge 120 has a substantially cylindrical shape and comprises a cylindrical main part 120A, a cylindrical proximal part 120B having a larger diameter than the main part 120A, and a cylindrical distal part 120C having a smaller diameter than the main part 120A. On the main part 120A, an NFC tag 125 is provided.

Figure 4:
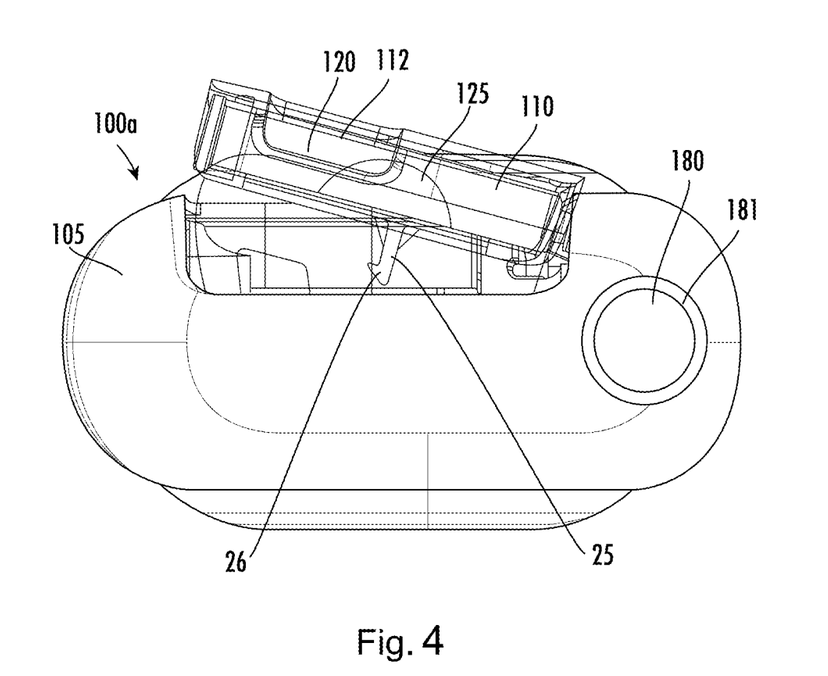
Figure 5:
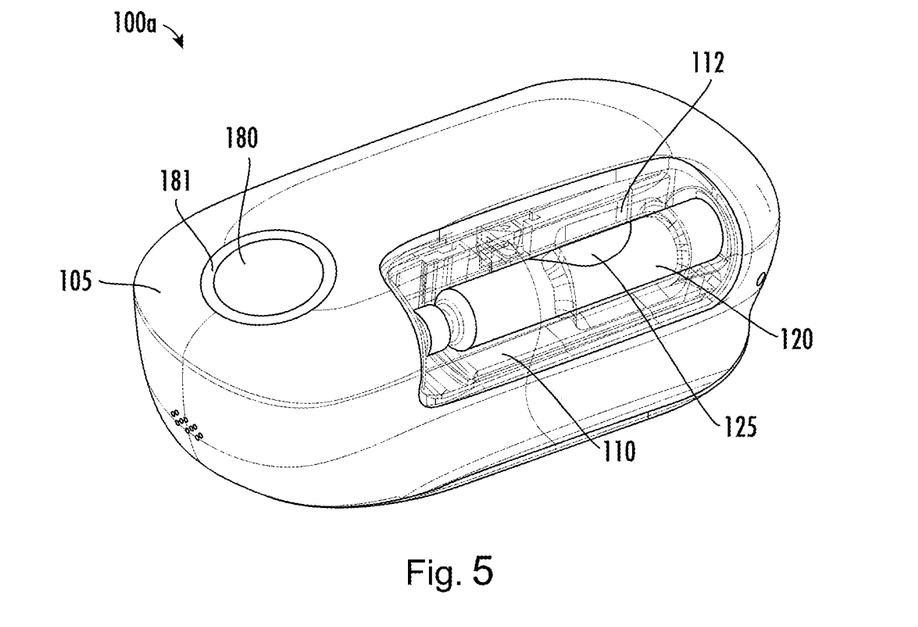

FIG. 4 shows the cartridge receiving unit 110 in the opened state after the cartridge 120 has been inserted into the cartridge receiving unit 110. FIG. 5 further shows the cartridge receiving unit 110 in the closed state after the cartridge 120 has been inserted into the cartridge receiving unit 110.

Figure 6:
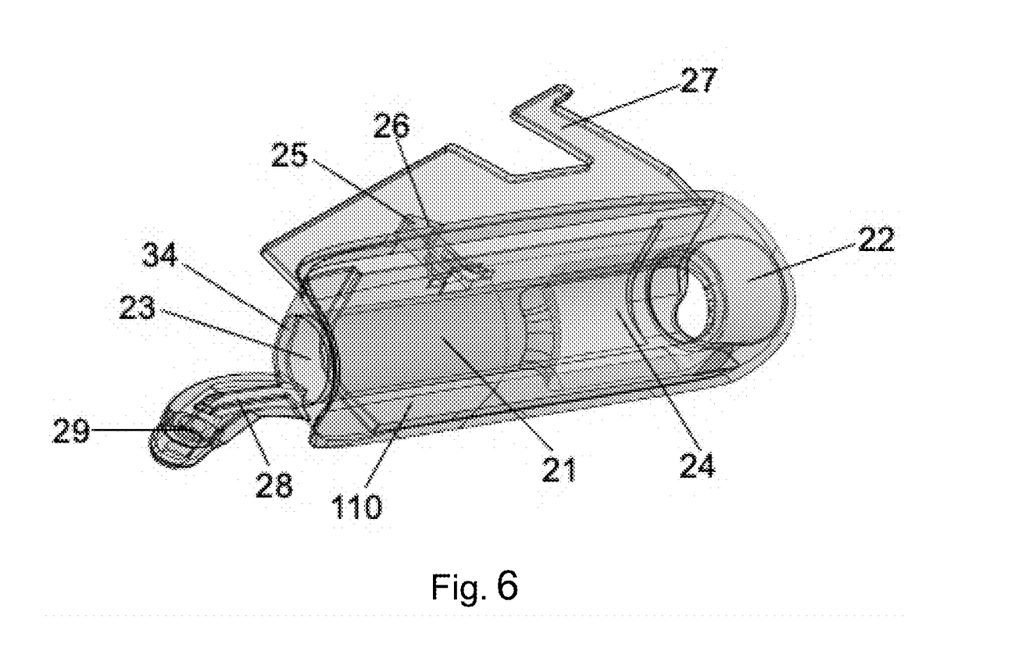

The cartridge receiving unit 110 is shown in more detail in FIG. 6. The cartridge receiving unit 110 comprises a substantially tubular shaped tube member 21 with a proximal opening 22 and a distal opening 23. The tube member 21 has a size and shape that fits the cartridge 120, i.e., a size to firmly hold the main part 120A of the cartridge 120, however, to still allow the cartridge 120 to be moved in the distal direction when a pushing force is applied to the proximal end of the cylindrical proximal part 120B.

At least one of the proximal opening 22 and the distal opening 23 has a diameter adapted to stop a movement of the cartridge 120. For example, the proximal opening 22 of the cartridge receiving unit 110 may have a smaller diameter than the proximal part 120B of the cartridge 120, or the distal opening 23 of the cartridge receiving unit 110 may have a smaller diameter than the main part 120A of the cartridge 120. In particular, the edge 34 of the distal opening 23 may act as a stopping member to stop a movement of the cartridge 120.

The cartridge receiving unit 110 further comprises a lock member 25, a guide element 27, and a hinge element 28. The lock member 25 comprises a first hook element 26 that is configured to be engaged with a counterpart hook element 62, which is provided in the injector device 100a (see FIG. 3). When the cartridge receiving unit 110 is in the closed position, the engagement of the first hook element 26 and the second hook element 62 prevents the cartridge receiving unit 110 from being moved to the opened position. The guide element 27 guides the movement of the cartridge receiving unit 110 between the opened position and the closed position. The hinge element 28 comprises a hole 29. Within the hole 29, a pin with a torsion spring (not shown in FIG. 6) may be provided. The torsion spring is adapted to cause a rotation of the cartridge receiving unit 110 from the closed position to the opened position around the pin.

Thus, under control of the control unit 140, the drive means 115 may release the spring of the torsion spring, which moves the cartridge receiving unit 110 in the opened position.

Figure 7:
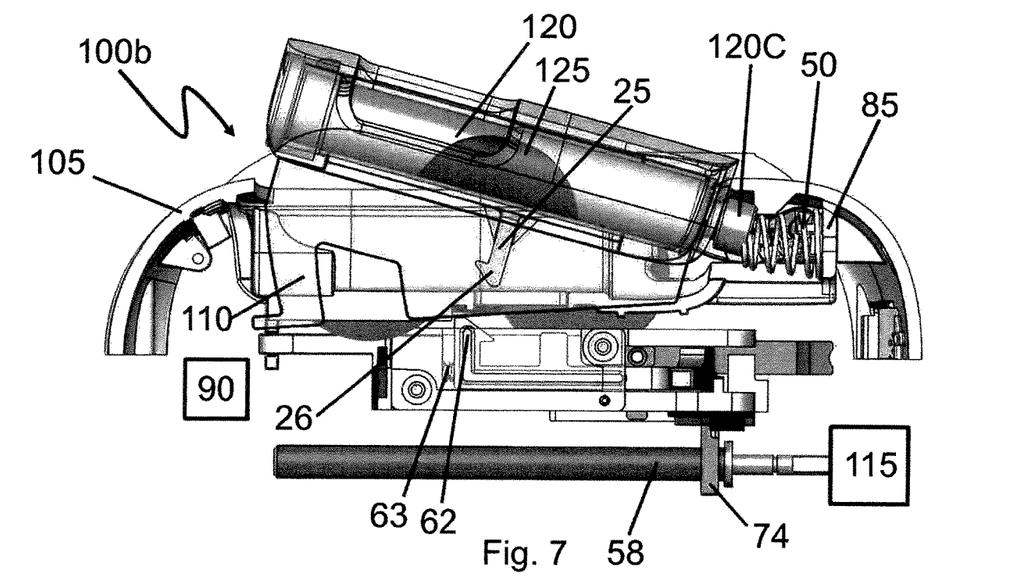
FIGS. 7 and 8 schematically show a third embodiment of an injector device.
Figure 8:
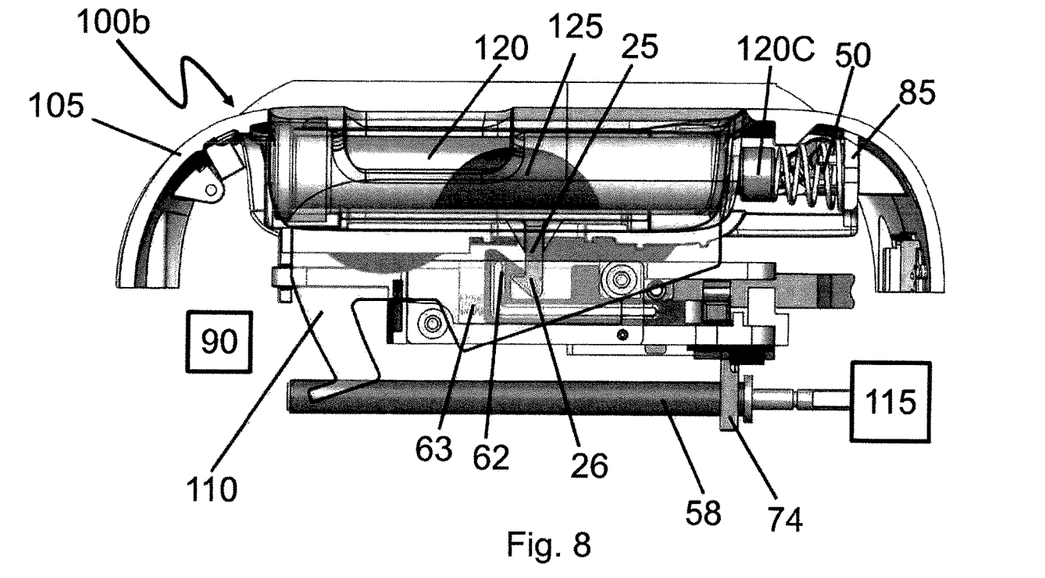

FIGS. 7 and 8 schematically show a third embodiment of an injector device 100b. The same elements of the third embodiment relate to the same elements of the first and second embodiments. In particular, the injector device 100b of the third embodiment may be the injector device 100a of the first embodiment or the injector device 100b of the second embodiment.

FIG. 7 shows the cartridge receiving unit 110 in the opened position. In FIG. 7, the cartridge 120 is loaded in the cartridge receiving unit 110. The counterpart hook element 62 is movably supported by a spring 63. In FIG. 7, the counterpart hook element 62 has been moved towards the spring 63, which has caused a compression of the spring 63. Thus, the cartridge receiving unit 110 can be rotated in the closed position shown in FIG. 8, in which the engagement of the counterpart hook element 62 with the first hook element 26 has taken place after a release of the spring 63. The movement of the counterpart hook element 62 in the direction towards the spring 63 has been caused by the drive means 115. Accordingly, the drive means 115 can also prevent a movement of the counterpart hook element 62 in the direction towards the spring 63.

Thus, the counterpart hook element 62 is adapted to prevent the cartridge receiving unit 110 from being moved from the closed position to the opened position. For this, determining means 90 are provided which are adapted to control the counterpart hook element 62 via the drive means 115. Specifically, the determining means 90 are adapted to control the counterpart hook element 62 via the drive means 115 to permanently prevent the cartridge receiving unit 110 from being moved from the closed position to the opened position.

FIGS. 7 and 8 further show a coil spring 50 that is supported at a wall element 85. When the cartridge 120 is inserted into the cartridge receiving unit 110, the distal part 120C of the cartridge 120 abuts the coil spring 50 so that the cartridge 120 may be moved within the cartridge receiving unit 110 towards the wall element 85, which compresses the coil spring 50. Within the coil spring 50 a septum needle 190 is provided (not shown in FIGS. 7 and 8), which pierces the septum 123 of the cartridge 120 when the cartridge 120 is moved towards the wall element 85. The movement of the cartridge 120 towards the wall element 85 is caused by the drive means 115 under control of the control unit 140.

The drive means 115 are mechanically coupled to a leadscrew 58. The leadscrew 58 comprises a driving gear (not shown in FIGS. 7 and 8) that can be driven, i.e., rotated, by the drive means 115. A nut 74 is provided on the leadscrew 58. The nut 74 comprises a female inner thread which fits the leadscrew 58 as a male thread so that a rotation of the driving gear by the drive means 115 causes a movement of the nut 74 along the leadscrew 58. For this, a guiding element is further provided (not shown in FIGS. 7 and 8) which guides the movement of the nut 74. A rotation of the driving gear by the drive means 115 in the opposite direction causes a movement of the nut 74 in the opposite direction along the leadscrew 58.

When the nut 74 is moved from a position at which the cartridge receiving unit 110 is closed in a direction away from the drive means 115, the nut 74 triggers a pivoted lock wheel (not shown in FIGS. 7 and 8). The lock wheel pushes the second hook element 62 towards the spring 63, which results in disengagement of the second hook element 62 and the first hook element 26. Thus, the cartridge receiving unit 110 can be opened. Thereafter, when the cartridge receiving unit 110 is closed, the second hook element 62 snaps and engages with the first hook element 26 so that the cartridge receiving unit 110 cannot be opened anymore.

Figure 9:
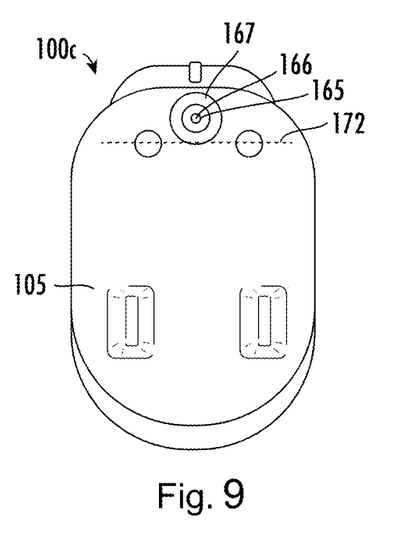
FIGS. 9 and 10 schematically show a fourth embodiment of an injector device.
Figure 10:
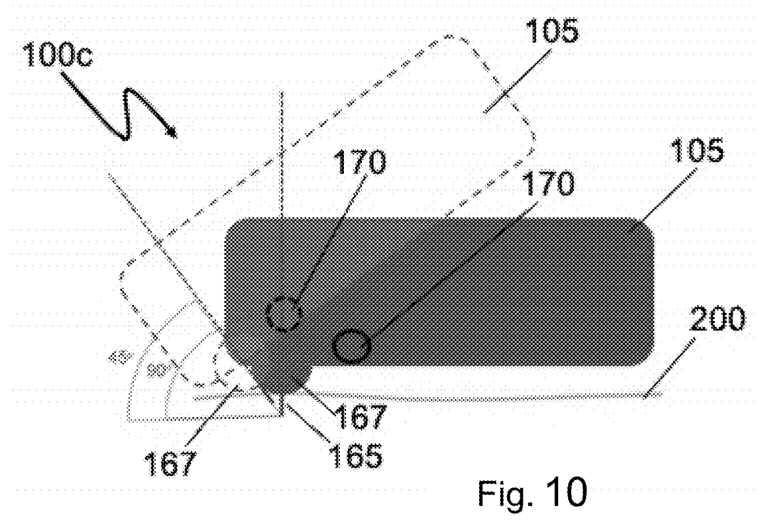

FIGS. 9 and 10 schematically show a fourth embodiment of an injector device 100c. The same elements of the fourth embodiment relate to the same elements of the first to third embodiments. In particular, the injector device 100c of the fourth embodiment may be the injector device 100 of the first embodiment, the injector device 100a of the second embodiment, or the injector device 100b of the third embodiment.

FIG. 9 schematically shows the injector device 100c from the bottom side, and FIG. 10 schematically shows a side-view of the injector device 100c. In particular, FIG. 10 shows the injector device 100c being placed on the skin 200 of a human or animal body. The dashed lines show the injector device 100c being partly removed from the skin 200 of the human or animal body.

The injector device 100c comprises at its bottom site a protrusion 167 that extends from the housing 105. The protrusion 167 has a cross-sectional shape of a segment of a circle. Through the protrusion 167, the skin needle 165 is ejected from the housing 105. When the skin needle 165 is retracted into the housing 105, it does not protrude from the housing 105 so that a user of the injector device 100c cannot be injured by the skin needle 165.

As can be seen from FIGS. 9 and 10, the first proximity sensor 170 and the second proximity sensor 172 are located at positions that are more central than the location of the skin needle 165. Specifically, a virtual line (shown as a dashed line in FIG. 9) connecting the first proximity sensor 170 and the second proximity sensor 172 does not cross the skin needle 165 in its ejected state. Moreover, the first proximity sensor 170 and the second proximity sensor 172 are located with the same distance from the skin needle 165.

Thus, only when the injector device 100c is correctly placed on the skin of a human or animal body, the first proximity sensor 170 sends the first proximity signal and the second proximity sensor 172 sends the second proximity signal. If only one proximity signal is received at the same time by the control unit 140, the control unit 140 knows that the injector device 100c is not correctly placed on the skin 200 of the human or animal body. Moreover, in the situation indicated by the dashed lines in FIG. 10, the injector device 100c is rotated by an angle of 45° clockwise around the location where the protrusion 167 is laid on the skin 200. In this case, the control unit 140 receives neither the first proximity signal nor the second proximity signal.

Moreover, in case the injector device 100c is not correctly placed on the skin 200, the lightening element 181 (see FIG. 2) may show a red color. Furthermore, when the injector device 100c is correctly placed on the skin 200, the lightening element 181 may show a green color.

Figure 11:
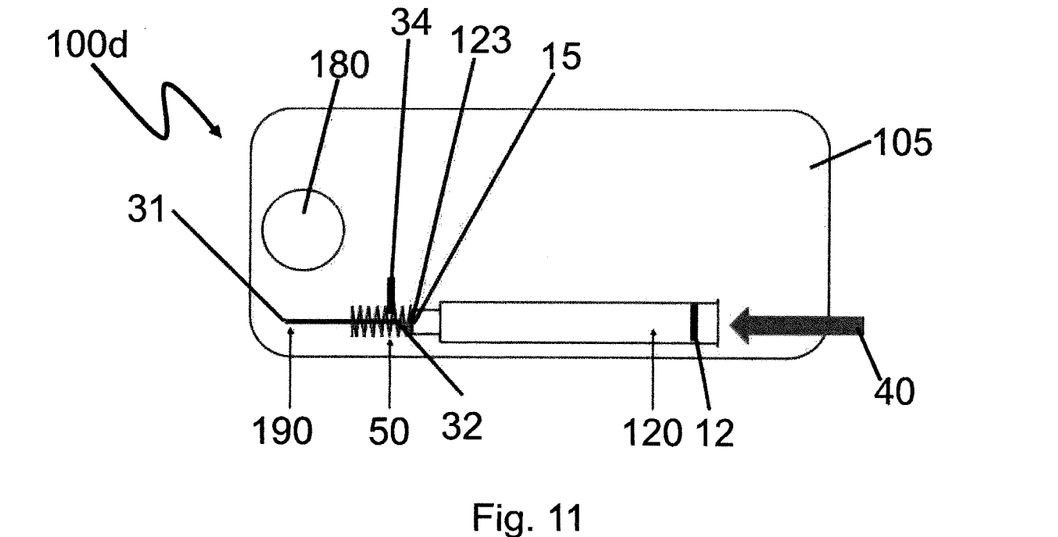
FIGS. 11 and 12 schematically show a fifth embodiment of an injector device.
Figure 12:
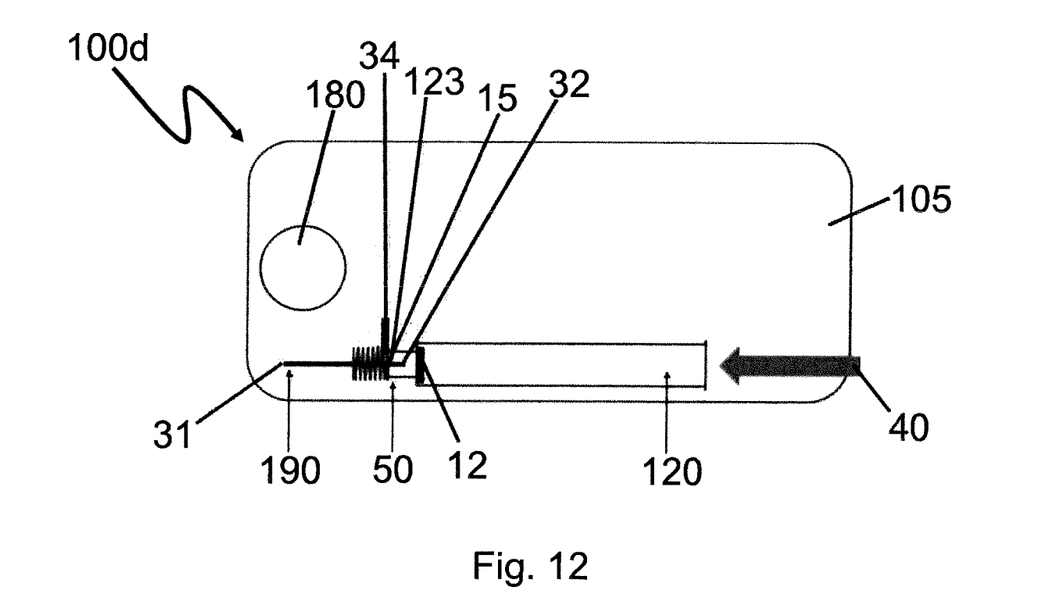

FIGS. 11 and 12 schematically show a fifth embodiment of an injector device 100d comprising a septum piercing mechanism. The same elements of the fifth embodiment relate to the same elements of the first to fourth embodiments. In particular, the injector device 100d of the fifth embodiment may be the injector device 100 of the first embodiment, the injector device 100a of the second embodiment, the injector device 100b of the third embodiment, or the injector device 100c of the fourth embodiment.

The injector device 100d comprises a cartridge 120, a cartridge receiving unit 110 (not shown in FIGS. 11 and 12), a hollow septum needle 190, a plunger rod 40 (schematically illustrated in FIGS. 11 and 12 by an arrow), and a coil spring 50. FIGS. 11 and 12 further schematically illustrate a housing 105 of the injector device 100d. Under control of the control unit 140, the drive means 115 drive the plunger rod 40 (not shown in FIGS. 11 and 12).

The cartridge 120 comprises a piston 12 that is movable from the proximal position shown in FIG. 11 to the distal position shown in FIG. 12. At its distal end, the cartridge 120 comprises a septum 123 which covers a fluid dispensing port 15. Upon movement of the piston 12 from the proximal position in the distal direction towards the distal position, in case the dispensing port 15 is opened, a drug is distally forced out of the dispensing port 15. However, in case the dispensing port 15 is closed by the septum 123 and the drug is stored in the cartridge 120, movement of the piston 12 from the proximal position in the distal direction towards the distal position causes a force on the entire cartridge 120 in the distal direction. FIGS. 11 and 12 further show a stopping member 34 adapted to stop the movement of the cartridge 120 in the distal direction at the end position. FIGS. 11 and 12 also show an initiation button 180 adapted to be pushed by a user in order to start the injection.

The septum needle 190 comprises a distal end 31 and a proximal end 32, and is immovably fixed in the injector device 100d. The proximal end 32 has a sharp tip end which is adapted to pierce the septum 123 such that the dispensing port 15 is opened. The cartridge 120 with the piston 12, the cartridge receiving unit 110 (not shown in FIGS. 11 and 12), the septum needle 190, the plunger rod 40, and the coil spring 50 are all arranged along the same axial line.

The coil spring 50 comprises a distal end and a proximal end, wherein the distal end is fixed in the injector device 100d such that a movement of the cartridge 120 in the distal direction compresses the coil spring 50, as can be seen from FIG. 12. The coil spring 50 surrounds the septum needle 190 such that before the movement of the cartridge 120 in the distal direction, the coil spring 50 keeps a distance between the proximal end 32 of the septum needle 190 and the septum 123. Thus, in the state before the movement of the cartridge 120 in the distal direction shown in FIG. 11, the distal end 31 of the septum needle 190 protrudes distally from the distal end of the coil spring 50, whereas the proximal end of the coil spring 50 protrudes proximally from the proximal end 32 of the septum needle 190.

When the plunger rod 40 is moved from the first position shown in FIG. 11 in the distal direction, it pushes the piston 12 in the distal direction. In particular, as long as the septum needle 190 has not pierced the septum 123, the movement of the piston 12 in the distal direction causes a movement of the piston 12 together with the entire cartridge 120 in the distal direction, i.e., the cartridge 120 is forced to slide within the cartridge receiving unit 110 (not shown in FIGS. 11 and 12) in the distal direction via the piercing state at which the proximal end 32 of the septum needle 190 pierces the septum 123.

After the septum 123 has been pierced by the septum needle 190, which causes the drug to be dispensed from the cartridge 120 through the distal end 31 of the septum needle 190, the cartridge 120 and the piston 12 still move with approximately the same speed until the movement of the cartridge 120 is stopped by the stopping member 34. In particular, the movement of the cartridge 120 in the distal direction ends with the situation shown in FIG. 12, in which the proximal end 32 of the septum needle 190 has pierced the septum 123, the coil spring 50 is compressed after being pushed by the distal end of the cartridge 120, the piston 12 is located at its most distal position, the plunger rod 40 is located at its most distal position (not shown in FIG. 12), and the drug has been dispensed via the dispensing port 15 through the hollow septum needle 190. Thus, at the end of the septum piercing process, the coil spring 50 is compressed such that the proximal end 32 of the septum needle 190 protrudes from the proximal end of the coil spring 50.

Accordingly, piercing of the septum 123 by the septum needle 190 may be independently controlled by the control unit 140, i.e., independently of the ejection of the skin needle 165. Thus, the control unit 140 can cause the needle ejection mechanism 160 to eject the skin needle 165 and can cause the piercing of the septum 123 by the septum needle 190 immediately before or simultaneously with the ejection of the skin needle 165.

Figure 13:
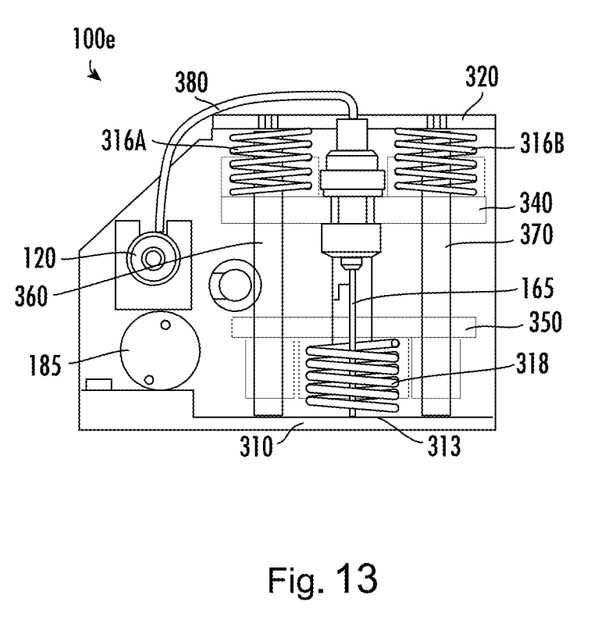
FIG. 13 schematically shows a sixth embodiment of an injector device with a needle ejection and retraction mechanism.

FIG. 13 schematically shows an injector device 100e with a needle ejection and retraction mechanism according to a sixth embodiment. The injector device 100e may comprise the same elements as any of the first to fifth embodiments. Thus, the same reference numbers relate to the same elements and any repeated explanation thereof is omitted.

In particular, FIG. 13 shows how a needle ejection and retraction mechanism may be installed in the injector device 100e and how a hollow skin needle 165 may be ejected into the skin of a human or animal body before the drug is dispensed from the cartridge 120 via a conduit 380 through the hollow skin needle 165. In the injector device 100e, the ejection and retraction of the skin needle 165 is controlled by the control unit 140 (not shown in FIG. 13) via the drive means 115.

The needle ejection and retraction mechanism is provided in the housing of the injector device 100e, which comprises a base plate 310 and a top plate 320. Between the base plate 310 and the top plate 320, two vertical rods 360 and 370 are foreseen. The outer surface of the base plate 310 is adapted to be placed on the skin of a human or animal body.

The injector device 100e comprises the hollow skin needle 165 having a needle tip 313 which is adapted to pierce the skin of a human or animal body, two compressed first springs 316A and 316B for ejecting the skin needle 165 out of the injector device 100e, and a second compressed spring 318 for retracting the skin needle 165 back into the injector device 100e. The two first springs 316A and 316B extend in parallel to an axis along which the skin needle 165 is ejected, and are provided between the top plate 320 and a first support element 340 which is connected to a proximal end of the skin needle 165. Specifically, movement of a nut 74 (not shown in FIG. 13; see FIGS. 7 and 8) releases the spring forces of the two compressed first springs 316A and 316B so that the skin needle 165 is caused to be pushed by the two first springs 316A and 316B out of the injector device 100e. For example, the movement of the nut 74 may cause a lever (not shown in FIG. 13) holding the first springs 316A and 316B to be removed so that the two first springs 316A and 316B cause an ejection of the first support element 340 together with the skin needle 165.

Upon ejection of the skin needle 165, the needle tip 313 protrudes from the outer surface of the base plate 310 (not shown in FIG. 13). The second spring 318 is provided between the base plate 310 and a second support element 350, and is adapted to retract the skin needle 165 back into the injector device 300.

FIG. 13 further shows the cartridge 120 which is connected via the conduit 380 to the proximal end of the hollow skin needle 165. Thus, the conduit 380 is adapted to establish a fluid path between the proximal end of the skin needle 165 and the cartridge 120. Specifically, the conduit 380 may be the fluid path 195 shown in FIG. 1.

FIG. 13 illustrates the injector device 100e comprising a needle ejection and retraction mechanism. However, in a modified embodiment, the injector device 100e may only comprise a needle ejection mechanism. For this, the second spring 318 may be removed from the injector device 100e.

Figure 14:
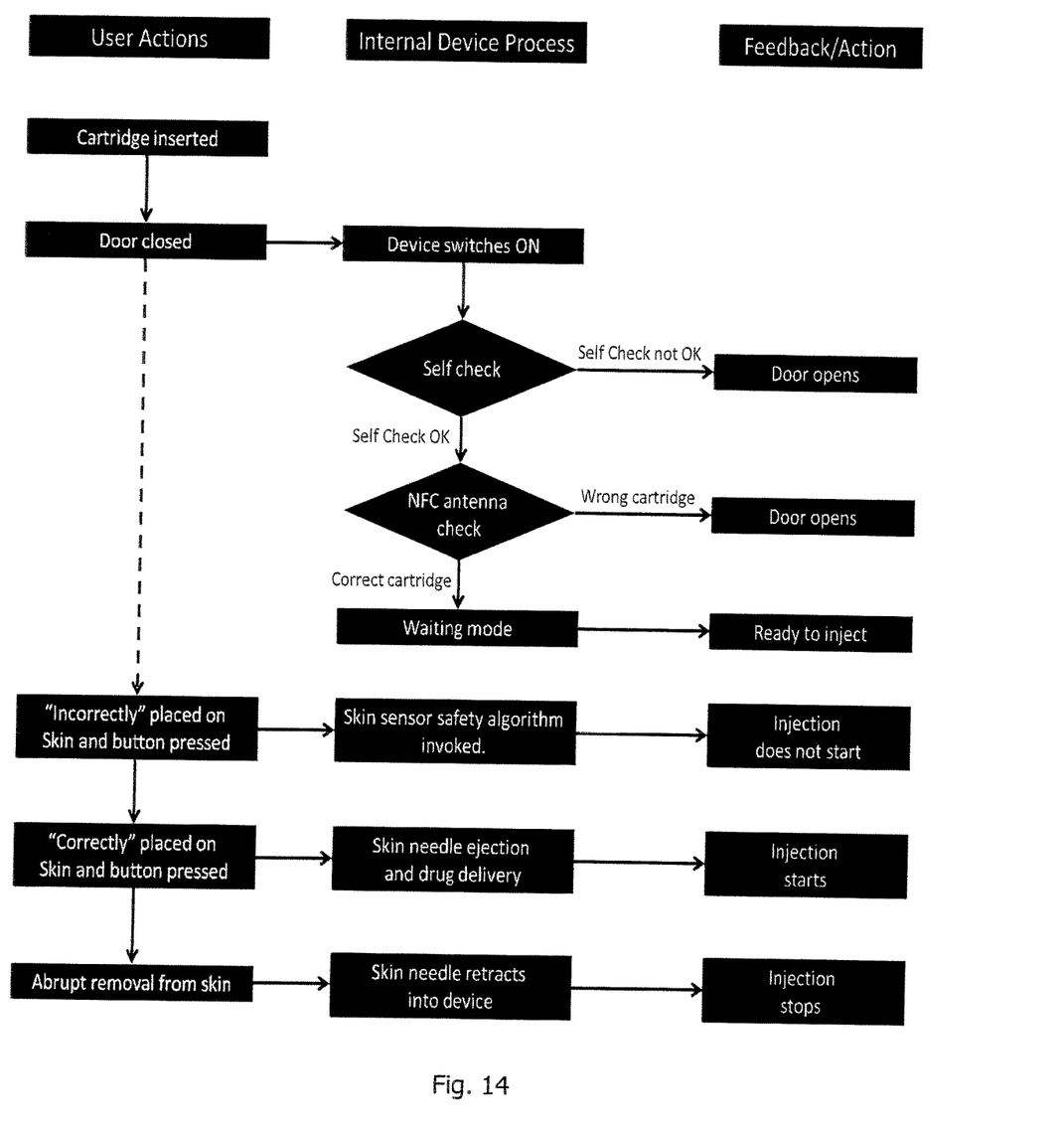
FIG. 14 shows a flow diagram of an exemplary safety scheme for an injector device.

FIG. 14 shows a flow diagram of an exemplary safety scheme. The safety scheme may be executed by any of the injector devices according to the first to sixth embodiments or any other injector device.

The flow diagram comprises three columns. The first column indicates actions by a user of the injector device, the second column indicates internal processes by the injector device in response to an action by the user, and column three indicates actions by the injector device.

Thus, an exemplary operation of the injector device starts with the user inserting a cartridge into the injector device. Thereafter, the user closes a door of the injector device. In response to the closing of the door, the injector device powers on. Thereafter, the injector device carries out a self-check, e.g., a self-test. In case the self-check is not successful, the door opens so that a user can remove the cartridge. In case the self-check is successful, the injector device carries out an NFC antenna check, i.e., checks the data stored in an NFC tag provided on the cartridge. In case the NFC antenna check provides the result that a wrong cartridge is inserted in the injector device, the door of the injector device is opened so that the cartridge can be removed from the injector device. In case the NFC antenna check is positive, the process continues to a waiting mode. From the waiting mode, the injector device may enter a status "ready to inject".

In case a user has incorrectly placed the injector device on the skin of a human or animal body, a skin sensor safety algorithm is invoked in the injector device, which results in the injector device not being started.

In case a user has correctly placed the injector device on the skin of a human or animal body, a skin needle ejection and drug delivery process is started, which results in a start of the injection.

Moreover, in case the injector device is removed (in particular, abruptly removed) from the skin of the human or animal body, a skin needle retraction process is started, which results in a stop of the injection.

The invention claimed is:

1. An injector device, comprising
access means configured to selectively allow and prevent a cartridge from being removed from the injector device;
a self-test unit configured to cause a self-test of at least one of an electronic component and an electronic assembly of the injector device; and
a control unit configured to control the access means to allow the cartridge to be removed from the injector device in case the self-test has failed, wherein the at least one of the electronic component and the electronic assembly of the injector device comprises a proximity sensor;
the self-test unit is configured to check as the self-test whether the proximity sensor operates correctly; and
in case the self-test of the proximity sensor has failed, the control unit causes a cartridge receiving unit of the injector device to be opened so that the cartridge can be removed from the cartridge receiving unit, and an injection operation of the injector device is not started until the proximity sensor passes the self-test.

2. The injector device according to claim 1, wherein
the control unit is configured to obtain cartridge data regarding a cartridge that is inserted in the injector device, check whether the cartridge data indicates that the inserted cartridge is not to be used with the injector device, and control the access means to allow the cartridge to be removed from the injector device in case the cartridge data indicates that the cartridge that is inserted in the injector device is not to be used with the injector device.

3. The injector device according to claim 2, wherein
the control unit is configured to control the access means to prevent the cartridge from being removed from the injector device in case the self-test was successful and the checked cartridge data indicates that the inserted cartridge can be used with the injector device.

4. The injector device according to claim 1, further comprising
a cartridge detector configured to determine whether a cartridge is inserted in the injector device, wherein
the control unit is configured to control the access means to allow a cartridge to be inserted in the injector device in case the cartridge detector has determined that no cartridge is inserted in the injector device.

5. The injector device according to claim 1, wherein
the access means comprises a cartridge receiving unit configured to receive and hold the cartridge, and
the control unit is configured to cause the cartridge receiving unit to at least partially protrude from a housing of the injector device so that a cartridge held in the cartridge receiving unit can be removed from the injector device in case the self-test has failed.

6. The injector device according to claim 1, further comprising
a hollow skin needle configured to be ejected from the injector device;
a proximity sensor configured to generate a proximity signal indicating that the injector device is placed on a skin of a human or animal body; and
ignition means configured to generate an ignition signal indicating that a user of the injector device has triggered the operation of the injector device, wherein
the control unit is configured to not cause an ejection of the skin needle from the injector device in case the control unit has obtained the proximity signal and the ignition signal, and the proximity signal has been continuously obtained from a power-on of the injector device until the ignition signal has been obtained.

7. The injector device according to claim 1, further comprising
a hollow skin needle configured to be ejected from the injector device;
a proximity sensor configured to generate a proximity signal indicating that the injector device is placed on a skin of a human or animal body; and
ignition means configured to generate an ignition signal indicating that a user of the injector device has triggered the operation of the injector device, wherein
the control unit is configured to not cause an ejection of the skin needle from the injector device in case the control unit has obtained the proximity signal and the ignition signal, and the ignition signal has been obtained within a predetermined period of time after the proximity signal has been obtained.

8. The injector device according to claim 1, further comprising
a hollow skin needle configured to be ejected from the injector device;
a proximity sensor configured to generate a proximity signal indicating that the injector device is placed on a skin of a human or animal body; and
ignition means configured to generate an ignition signal indicating that a user of the injector device has triggered the operation of the injector device, wherein
the control unit is configured to not cause an ejection of the skin needle from the injector device in case the control unit has obtained the proximity signal and the ignition signal, and the proximity signal has been obtained within a predetermined period of time after a point of time when the access means has prevented the cartridge from being removed from the injector device.

9. The injector device according to claim 1, further comprising
a first proximity sensor configured to generate a first proximity signal indicating that the injector device is placed on a skin of a human or animal body; and
a second proximity sensor configured to generate a second proximity signal indicating that the injector device is placed on a skin of a human or animal body, wherein the control unit is configured to determine that the injector device has been placed on a skin of a human or animal body based on the first proximity signal and the second proximity signal.

10. The injector device according to claim 9, wherein the control unit is configured to determine that the injector device has been placed on a skin of a human or animal body when the first proximity signal and the second proximity signal are obtained at a same time.

11. The injector device according to claim 9, further comprising a hollow skin needle configured to be ejected from the injector device, wherein a virtual line connecting the first proximity sensor and the second proximity sensor does not cross the skin needle in its ejected state.

12. The injector device according to claim 11, wherein the first proximity sensor and the second proximity sensor are located with a same distance from the skin needle, and/or the first proximity sensor and the second proximity sensor are located closer to the center of the injector device than the skin needle.

13. The injector device according to claim 9, further comprising a hollow skin needle configured to be ejected from the injector device, wherein the control unit is configured to determine based on the first proximity signal and the second proximity signal whether the injector device has been removed from the skin of the human or animal body, and cause a retraction of the skin needle into the injector device in response to the control unit determining that the injector device has been removed from the skin of the human or animal body.

14. The injector device according to claim 1, further comprising a hollow skin needle configured to be ejected from the injector device; and a septum needle configured to pierce a septum of the cartridge inserted into the injector device, wherein the control unit is configured to cause an ejection of the skin needle and a piercing of the septum by the septum needle immediately before or simultaneously with the ejection of the skin needle.

* * * * *